United States Patent [19]

Sloma

[11] Patent Number: 4,663,280

[45] Date of Patent: May 5, 1987

[54] EXPRESSION AND SECRETION VECTORS AND METHOD OF CONSTRUCTING VECTORS

[75] Inventor: Alan Sloma, New York, N.Y.

[73] Assignee: Public Health Research Institute of the City of New York, New York, N.Y.

[21] Appl. No.: 558,547

[22] Filed: Dec. 2, 1983

Related U.S. Application Data

[63] Continuation-in-part of Ser. No. 496,229, May 19, 1983, abandoned.

[51] Int. Cl.$^4$ .................... C12R 1/125; C12R 1/085; C07H 21/04; C12N 15/00; C12N 1/20; C12N 1/00; C12P 21/00; C12P 21/02; C12P 21/04; C12P 19/34

[52] U.S. Cl. ....................... 435/68; 435/70; 435/71; 435/91; 435/172.3; 435/253; 435/317; 435/834; 435/839; 536/27; 935/29; 935/48; 935/49; 935/74

[58] Field of Search .................. 435/68, 70, 172.3, 71, 435/91, 253, 834, 839, 317; 536/27; 935/41, 29, 48, 49, 74

[56] References Cited

FOREIGN PATENT DOCUMENTS 0063494 11/1982 European Pat. Off. .
0063953 12/1982 European Pat. Off. .

OTHER PUBLICATIONS

Lamper et al, "Penicillinase and the Secretion of Proteins by Bacilli", in *Molecular Cloning and Gene Regulation in Bacilli*, Ganesan et al (ed.), Academic Press, 1982, New York, pp. 99-109.

Chang et al, "Expression of Eukaryotic Genes in *Bacillus Subtilis*", in *Genetic Engineering Techniques: Recent Developments*, Huang et al (ed.), Academic Press, 1982, New York, pp. 243-250.

Ratzkin et al, "Expression in *Escherichia Coli* of Biologically Active Enzyme by a DNA Sequence Coding for the Human Plasminogen Activator Urokinase", Proc. Natl. Acad. Sci. USA 78:3313 (1981).

Bollen et al, "Expression in *Escherichi Coli* of Urokinase Antigenic Determinants", Biochem. Biophys. Res. Comm. 103:391 (1981).

Birnboim, H. C. and Doly, J. (1979), Nucleic Acids Res. 7, 1513-1523.

Blobel, G. and Dobberstein, D. (1975), J. Cell Biol. 67, 835-851.

Chang, S., Gray, O., Ho, D., Kroyer, J., Chang, S., McLaughlin, J. and Mark, D. (1982) in *Molecular Cloning and Gene Regulation in Bacilli*, Ganesan, A. T., Chang, pp. 159-169.

Contente, S. and Dubnau, D. (1979), Mol. Gen. Genet. 167, 251-258.

Dubnau, D., and Davidoff-Abelson, R. (1971), J. Mol. Biol. 56, 209-221.

Emr, S. D., Hall, M. N. and Silhavy, T. J. (1980), J. Cell. Biol. 86, 701-711.

Goeddel, D. V., Shepard, H. M., Yelverton, E., Leung, D., Crea, R., Sloma, A. and Pestka, S. (1980), Nucleic Acids Res. 8, 4057-4074.

Gray, O. and Chang, S. (1981), J. Bacteriol. 145, 422-428.

Gryczan, T. J. (1982), in *The Molecular Biology of the Bacilli*, Dubnau, D., Ed., pp. 307-329, Academic Press, New York.

Gryczan, T. J., Contente, S. and Dubnau, D. (1980), Mol. Gen. Genet. 177, 459-467.

(List continued on next page.)

*Primary Examiner*—James Martinell
*Attorney, Agent, or Firm*—Brumbaugh, Graves, Donohue & Raymond

[57] ABSTRACT

The present invention relates to an expression and secretion vector which comprises the signal and promoter sequence of the *Bacillus cereus* (herein "*B. cereus*") gene which codes for penicillinase and to the construction of vectors and the use of the vectors in the expression and secretion of one or more exogenous polypeptides in microorganisms for example, *B. subtilis.*

16 Claims, 6 Drawing Figures

OTHER PUBLICATIONS

Gryczan, T. J. and Dubnau, D., (1982), Gene 20, 459–469.

Gryczan, T. J. and Dubnau, D. (1978), Proc. Nat. Acad. Sci. USA 75, 1428–1432.

Hardy, K., Stahl, S. and Kupper, H. (1981), Nature 293, 481–483.

Harris, T. J. R., Lowe, P. A., Lyons, A., Thomas, P. G., Eaton, M. A. W., Millican, T. A., Patel, T. P., Bose, C. C., Carey, N. H. and Doel, M. T. (1982), Nucleic Acids Res. 10, 2177–2187.

Josefsson, L. and Randall, L. L. (1981), Cell 25, 151–157.

Koqut, M., Pollack, M. R. and Tridgell, E. J. (1956), Biochem. J. 62, 391–401.

Lawn, R. M. Adelman, J., Bock, S. C., Franke, A. E., Houck, C. M., Najarian, R. C., Seeburg, P. H. and Wion, K. L. (1981), Nucleic Acids Res. 9, 6103–6114.

Maxam, A. M. and Gilbert, W. (1980), Methods Enzymol. 65, 499–560.

Neugebauer, K., Sprengel, R. and Schaller, H. (1981), Nucleic Acids Res. 9, 2577–2588.

Neilsen, J. B. K. and Lampen, J. O. (1982), J. Biol. Chem. 257, 4490–4495.

Palva, I., Pettersson, R. F., Kalkkinen, N., Takkinen, K. and Kaariainen, L. (1981), Gene 15, 43–51.

Palva, I., Sarvas, M., Lehtovaara, P., Sibakov, M. and Kaariainen, L. (1982), Proc. Nat. Acad. Sci. USA 79, 5582–5586.

Pennica, D., Holmes, W. E., Kohr, W. J., Harkins, R. N., Vehar, G. A., Ward, C. A., Bennett, W. F., Yelverton, E., Seeburg, P. H., Heyneker, H. L., and Goeddel, D. V., Nature 301, 214 (1983).

Sherratt, D. J. and Collins, J. F. (1973), J. Gen. Microbiol. 76, 217–230.

Talmadge, K., Kaufman, J. and Gilbert, W. (1980), Proc. Nat. Acad. Sci. USA 77, 3988–3992.

Yang, M., Galizzi, A. and Henner, D. (1983), Nucleic Acids Res. 11, 237–249.

Palva, I., Lehtovaara, P., Kaariainen, L., Sibakov, M., Cantell, K., Schein, C. H., Kashiwagi, K., and Weissmann, C., (1983), Gene, 22, 229–235.

Federation of European Biochemical Societies, vol. 161, pp. 195–200 (1983).

```
GTATACATGTAATCTACTAGTACAGGTGGTCCAAGCAAATTAGAATACTTTTCTCAGGAAGAGAACCTGTTTATATAAAGCCATTTATAAGTAAA       99
AccI

AAAATGAAATGAAATAAGAGATAGTGGCGATCATAGCTACTACTATCTCCTATTTGTAATAATTCTCATACTAGCTATAAATTTTTCAGTTTATGA      198
                                                                  -35                   -10 f-MetIleLeuLysAsnLysArgMetLeuLys
ACAAATTGGTTCGGTGATTGTCTATTATGTGTACGTATAAAAAGGTGCTAAAAATTTGAAGGAATGATGATTTGAAAAATAAGAGGATGCTAAAA        296
                                                                            S.D.

IleGlyIleCysValGlyIleLeuGlyLeuSerIleThrSerLeuGluAlaPheThrGlyGluSerLeuGlnValGluAlaLysGluLysThrGlyGln
ATAGGAATATGCGTTGGTATATTAGTTTAAGTATTACAAGCCTAGAAGCTTTACAGGAGAGTCACTGCAAGTTGAAGCGAAAGAAAAGACTGGACAA      395
                                                        HindIII
```

FIG. 2-1

```
ValLysHisLysAsnGlnAlaThrHisLysGluPheSerGlnLeuGluLysLysPheAspAlaArgLeuGlyValTyrAlaIleAspThrGlyThrAsn
GTGAAACACAAAATCAGGCAACGCATAAAGAGTTCTCTCAACTTGAGAAAAAATTTGATGCTCGATTAGGTGTATATGCGATTGATACTGGTACAAAT     494

GlnThrIleSerTyrArgProAsnGluArgPheAlaSerThrTyrLysAlaLeuAlaGlyValLeuLeuGlnAsnSerIleAspSer
CAAACAATCTCTTATCGACCTAACGAAAGATTTGCCTTCGCATCAACATACAAGGCTTTAGCCGCGGGAGTATTACTACAGCAAACTCAATTGATTCA     593

LeuAsnGluValIleThrTyrThrLysGluAspLeuValAspTyrSerProValThrLeuLysHisValAspThrGlyMetLysLeuGlyGluIleAla
TTAAATGAAGTAATCACATATACGAAAGAAGACTTAGTGGATTATTCACCTGTTACAGAGAAACATGTAGATACTGGAATGAAACTAGGAGAAATTGCA     692

GluAlaAlaValArgSerSerAspAsnThrAlaGlyAsnIleLeuPheAsnLysIleGlyGlyProLysGlyTyrGluLysAlaLeuArgHisMetGly
GAGGCAGCTGTCGTTCAGTGATAATACTGCAGGGAACATTTTATTTAATAAAATAGGAGGACCGAAAGGATATGAAAAAGCGCTTAGGCATATGGGG     791
     PvuII              PstI                                                 AvaII
```

FIG. 2-2

```
AspArgIleThrMetSerAsnArgPheGluThrGluLeuAsnGluAlaIleProGlyAspIleArgAspThrSerThrAlaLysAlaIleAlaThrAsn
GATCGGATTACTATGTCTAATCGCTTTGAAACAGAATTAAACGAAGCTATTCCAGGAGACATTCGTGACACTAGTACAGCAGCGAAAGCTATTGCTACGAAT   890

LeuLysAlaPheThrValGlyAsnAlaLeuProAlaGluLysArgLysIleLeuThrGluTrpMetLysGlyAsnAlaThrGlyAspLysLeuIleArg
CTTAAAGCTTTTACGGTCCGGAAATGCACTTCCAGCTGAAAAACGTAAATTCTTACAGAGTGGATGAAAGGAAATGCTACAGGGGACAAACTTATTAGA   989
       HindIII                             PvuII AlaGlyIleProThrAspTrpValValGlyAspLysSerGlyTyrGlyAlaGlySerTyrArgAsnAspIleAlaValValTrpProAsnSerAla
GCAGGCATACCAACTGACTGGGTAGTTGGAGATAAATCAGGTGCTGGTAGTTACGGGACAAGAAATGATATTGCTGTCGTTTGGCCTCCAAATAGTGCA  1088

ProIleValLeuIleSerSerLysAspGlyGluLysGlnLeuIleAlaGluAlaIleTyrAsnAspIleAsnAspGlnLeuIleAlaGluAlaThrLysValIleValLysGlySer
CCAATTATCGTATTAATTTCATCGAAAGATGAGAAAGAGCCAATCTATAATGATCAACTGATTGCGGAGGCAACTAAAGTTATAGTTAAAGGCTTTAG  1187

GTAATCGTGTTTCGTTTCGCGTTTTTGAT  1218
```

FIG. 2-3

```
GTATACATGGTAATCTACTAGTACAGGTGGTTCCAAGCAAATTAGAATACTTTCTCAGGAGAGAACCTGTTTATATAAAGCCATTTATAAGTAAA
     ──→
     AccI

AAAATGAAATGTGAAATAAGAGATAGTGGCCGATCATAGCTACTACTCTCCTATTTTGTTAATAATTCTCCATACTAGCTATAAATTTTTCAGTTTATGA
                                                   ─────                           ─────
                                                     -35                             -10 f-MetIleLeuLysAsnLysArgMetLeuLys
ACAAATTGGTTCGTGATTGTCTATTATGTGTACGTATAAAAGGTCTAAAAATTTGAAGGAATGATGATTTGAAAAATAAGAGAGATGCTAAAA
                                                                  ───
                                                                  S.D.

IleGlyIleCysValGlyIleLeuGlyLeuSerIleThrSerLeuGluAlaPheThrGlyGluSerLeuGlnValGlnAlaLysGluLysThrGlyGln
                                                                                 ──→
ATAGGAATATGCGTTGGTTATATTAGTTTTAAGTATTACAAGCTTTACAGGAGAGTCACTGCAAGTTGAAGCGAAAGAAAAGACTGGACAA
                                       ───────
                                        HindIII
```

*FIG. 3*

EXPRESSION AND SECRETION VECTORS AND METHOD OF CONSTRUCTING VECTORS

This application is a continuation-in-part of application Ser. No. 496,229 filed on May 19, 1983, now abandoned.

BACKGROUND OF THE INVENTION

The present invention relates to an expression and secretion vector which comprises a specific segment of the *Bacillus cereus* (herein "*B. cereus*") gene which codes for penicillinase on a plasmid and to the construction of vectors and the use of the vectors in the expression and secretion of one or more exogenous polypeptides in microorganisms for example, *B. subtilis*.

The term gene as used herein is a chromosomal segment that codes for a single polypeptide chain or RNA molecule. Protein as used herein refers to a macromolecule composed of one or more polypeptide chains, each possessing a characteristic amino acid sequence and molecular weight.

Bacteria are commonly divided into two major categories: gram-positive and gram-negative. The basis for this distinction is the structure of the cell envelope. In gramnegative bacteria, for example, *E. coli*, the cell envelope consists of three major layers: an inner cytoplasmic membrane, a thin peptidoglycan layer, and an outer membrane. Gram-positive organisms, for example, *B. subtilis*, have a cytoplasmic membrane and a thick cell wall. These different structures affect how the bacteria secretes protein. Because of the three layers in the cell envelope, very few proteins are secreted outside the cell envelope in gram-negative organisms.

The mechanism of transfer of proteins across cell membranes was first described in a eukaryotic system by Blobel, G. and Dobberstein, D., (1975) J. Cell Biol. 67, 835-851. They showed that a protein which is secreted from a cell is synthesized initially as a larger protein precursor with 15-30 additional amino acids at the $NH_2$-terminus as compared to the secreted protein. These additional terminal amino acids on the protein are called the "signal peptide" and help direct the transfer of the protein across the cell membrane. The DNA sequence that codes for this peptide is called the "signal sequence". The signal peptide is cleaved from the protein at a specific point during the protein secretion process. Most secreted eukaryotic proteins that have been studied to date have a signal peptide.

In *E. coli*, a prokaryotic cell, some proteins have also been found to have signal peptides at the $NH_2$-terminus. Examples are the maltose-binding protein, the arabinase binding protein, alkaline phosphatase, and $\beta$-lactamase; Josefsson, L. and Randall, L. L., (1981) Cell 25, 151-157; Emr, S. D., Hall, M. N. and Silhavy, T. J. (1980) J. Cell. Biol. 86, 701-711. After the protein is processed, in *E. coli*, these proteins are secreted into the periplasmic space which is between the inner and outer membranes of the cell.

Bacilli and other gram-positive organisms are, however, known to secrete proteins directly into the extracellular medium. The genes for some of the major secretion proteins in Bacilli have already been cloned and DNA sequencing has identified the amino acids in the signal peptide. These include amylase from *B. amyloliquefaciens;* Palva, I. et al. (1981), *B. subtilis;* Yang, M., Galizzi, A. & Henner, D., (1983) Nucleic Acids Res. 11, 237-249 Gene 15, 43-51 and penicillinase from *B. licheniformis;* Neugebauer, K., Sprengel, R. & Schaller, H., (1981) Nucleic Acids Res. 9, 2577-2588. These proteins also have a typical signal peptide that, in the gram-positive Bacilli organism, direct the secreted protein outside the cell.

Cloning of a gene can be defined as a process that involves moving a gene from one cell into a new host's cell, sorting those transformed host cells, and selecting the cells having the particular moved gene from the cell mixture. The gene of interest is moved into a host by means of a vector (carrier) which, for example, can be a large DNA molecule, such as a plasmid. A vector is defined as a DNA molecule known to replicate autonomously in a host cell, to which a foreign segment of DNA may be introduced in order to bring about its replication. A plasmid is defined as an extra-chromosomal, independently replicating small circular DNA molecule. The host and the vector used to clone a gene is referred to as a host vector (Hv) system.

There have been many reports of successful cloning of eukaryotic genes in *E. coli*, for example, human serum albumin by Lawn, R. M. et al., (1981) Nucleic Acids Res. 9, 6103-6114; calf rennin; Harris, T. J. R. et al., (1982) Nucleic Acids. Res, 10, 2177-2187 and plasminogen activator; Pennica, D. et al. (1983) Nature 301, 214-221. These proteins all have signal sequences and are normally secreted by the host eukaryotic cell. Because the signal peptide from a foreign gene will also be recognized by the *E. coli* cell, as shown by Talmage, K., Kaufman, J. & Gilbert, W. (1980) Proc. Nat. Acad. Sci. USA 77, 3988-3992 these expressed foreign proteins are found in the periplasm of the *E. coli* organism if their signal sequence is not removed. This usually makes purification of the secreted proteins more difficult. Therefore, a cloning strategy in *E. coli* has been developed where the DNA that codes for the signal peptide is removed completely and the gene coding for the mature protein is connected at the 3' end of a bacterial promoter. This has been done with interferon, plasminogen activator and insulin. This results in the accumulation of the foreign protein in the cytoplasm of *E. coli*, where it can be purified easier than if it accumulated in the periplasm.

The most widely studied gram-positive organism is *B. subtilis*. It has many advantages over *E. coli* for the development of a cloning system. Since it is not associated with any human diseases it is a nonpathogen. Unlike *E. coli*, *B. subtilis* does not produce endotoxin. This greatly simplifies the purification problems which are inherent in the use of *E. coli* to produce products for medical or veterinary use. *B. subtilis* is also a fermentation organism which is grown routinely on an industrial scale. These factors coupled with its potential to secrete useful foreign proteins into the extracellular medium make the organism well suited for a cloning-expression system.

Many *B. subtilis* cloning vectors have already been established and are described by Gryczan, T. J. (1982) in the Molecular Biology of the Bacilli, Dubnau, D., ed., pp. 307-329, Academic Press, N.Y. which is incorporated herein by reference. These cloning vectors which make it possible to carry new genes to *B. subtilis* cells, are plasmids which have many unique restriction sites, and encode selectable antibiotic resistance markers which are useful for isolation purposes. The use of these *B. subtilis* vectors and the optimization of plasmid cloning in *B. subtilis* as described by Gryczan, T. J., Contente, S. & Dubnau, D. (1980) Mol. Gen. Genet.

177, 454-467 has permitted the cloning of heterologous or foreign genes in *B. subtilis*. The first report of the cloning of such a heterologous gene in *B. subtilis* encoded the core antigen (HBV) of hepatitis B and the major antigen (VPI) of foot and mouth disease virus; Hardy, K., Stahl, S. and Kupper, H. (1981), Nature 293, 481–483. Both of these heterologous genes were cloned into the erythromycin gene of pBD9, which is a *Bacillus subtilis* plasmid chimera with multiple antibiotic resistance; Ehrlich, S. P. et al. (1978) In "Genetic with Multiple Antibiotic Resistance: H. W. Boyer and S. Nicosia, eds., pp. 25-32 and Gryczan, T. J. and Dubnau, D. (1978) Proc. Nat. Acad. Sci. USA 75, 1428–1432. The result of this work was a *B. subtilis* strain that produced fusion proteins (part erythromycin resistance protein, part viral antigen) in the *B. subtilis* cell. The erythromycin resistance protein is not a secretory protein.

The first report of the cloning of eukaryotic genes in *B. subtilis* came from Chang, S. et al., (1982) In Molecular Cloning and Gene Regulation in Bacilli, Ganesan, A. T. et al., ed., pp. 159–169, Acadamic Press, New York. They had previously cloned the penicillinase gene from *Bacillus licheniformis* (herein "*B. licheniformis*") in *B. subtilis;* Gray, O. and Chang, S. (1981) Bacteriol. 145, 422–428. The gene for human insulin was cloned and expressed in *B. subtilis* by joining the first third of the *B. licheniformis* penicillinase gene with the preproinsulin gene. This resulted in the secretion of a fusion protein into the media that was detected by antibodies to insulin. The *B. licheniformis* penicillinase promoter was also used to express β-interferon (IF) in *B. subtilis*. In this case, the *B. licheniformis* penicillinase gene including the signal peptide was removed, and the gene coding for the mature β-IF (interferon) was fused at the 3' end of the penicillinase promoter. The resulting plasmid was used to transform *B. subtilis* cells. β-interferon was detected within the *B. subtilis* cells that were transformed with this plasmid containing the β-IF sequence.

It was also shown that a Bacillus signal peptide could direct the secretion of foreign protein (β-lactamase) outside the cell in *B. subtilis*. Palva, I. et al., (1982) Proc. Nat. Acad. Sci USA 79, 5582-5586 used the α-amylase promoter and signal sequence from *Bacillus amyloliquefaciens* (herein "*B. amyloliquefaciens*") to successfully express and secrete *E. coli* β-lactamase in *B. subtilis*. The amylase promoter and signal was joined to the start of the mature *E. coli* gene coded for β-lactamase from which the *E. coli* β-lactamase signal sequence was removed. Proper fusions to the mature gene resulted in the secretion and correct processing by *B. subtilis* of the β-lactamase protein into the outside media.

The prior art has shown the use of *B. licheniformis* and *B. amyloliquefaciens* signals and promoters in *B. subtilis* cloning vectors to express and secrete foreign protein by *B. subtilis*.

SUMMARY OF THE INVENTION

A vector has now been constructed which allows a host microorganisms including *B. subtilis* cells to secrete one or more exogenous (herein sometimes referred to as "foreign") polypeptides or proteins into the culture medium. The vector comprises a plasmid capable of replicating in the host microorganism and the signal sequence and promoter sequence of the *B. cereus* gene which codes for pencillinase said signal sequence having a restriction site at or near the end of the signal sequence to which one or more heterologous genes which code for one or more exogenous polypeptide can be linked.

The *B. cereus* gene which codes for penicillinase was cloned and identified. The signal sequence and promoter sequence of the gene was isolated and a restriction site is identified or constructed or identified on the signal sequence in order to link the signal and promoter sequence to one or more heterologous genes which code for one or more exogenous polypeptide. The vectors described herein are constructed for use in transforming both *B. subtilis* and other microorganisms.

The following detailed examples illustrate how the preferred vectors were constructed and are used in *B. subtilis* to express and secrete one or more exogenous polypeptide or protein into the culture medium. These examples are intended only for illustration and are not intended to limit the scope of the invention in any way.

BRIEF DESCRIPTION OF THE DRAWINGS

FIG. 2 shows the sequence of the structural and regulatory elements of the penicillinase gene in plasmid pAS7.

FIG. 3 shows the promoter and signal sequences of *B. cereus* penicillinase.

DESCRIPTION OF THE PREFERRED EMBODIMENTS

Figure 1:
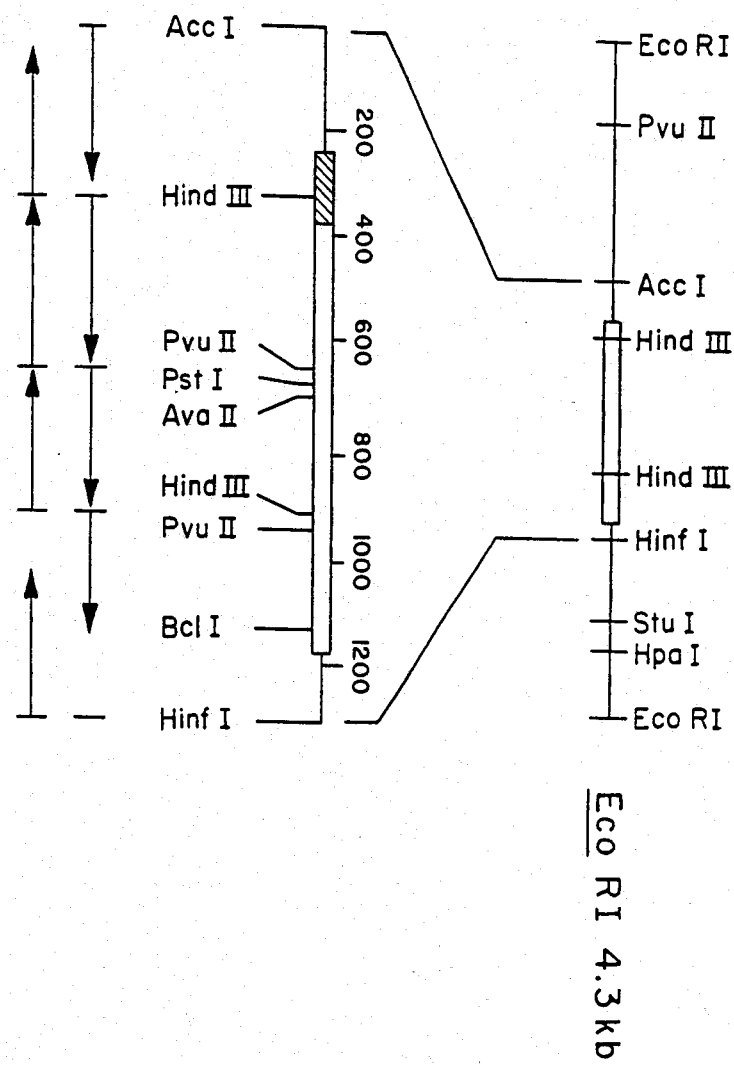
FIG. 1 shows a restriction map of the pAS7 plasmid DNA and the EcoRI 4.3 kilobase fragment thereof.

A. Isolation of Total DNA from *B. cereus* 569H 100 ml of VY, prepared as described by Dubnau, D. and Davidoss-Abelson, R., J. (1971) Mol. Biol. 58, 209-221 was inoculated with 1 ml (about $1 \times 10^{10}$ cells) of an overnight culture of *B. cereus* 569H, in VY medium (ATCC #13061) a constitutive producer of penicillinase described by Kogut, M., Pollack, M. R., Tridgell, E. J. (1956), Biochem. J. 62, 391–401. When the culture reached a Klett of 250 ($2 \times 10^9$ cells/ml), the cells were centrifuged and washed with 50 ml of LM (0.05M NaCl, 0.1M EDTA pH 6.9). The cells were again centrifuged and frozen. DNA was prepared by the following modified procedure described by Dubnau, D. and Davidoff-Abelson, R. (1971) J. Mol. Biol. 58, 209–221. The frozen *B. cereus* 569H cells were resuspended in 10 ml of LM and 5 mg of egg white lysozyme (Sigma, 48,000 U/mg) were added. The solution was incubated at 37° C. for 30 minutes, 1 ml of 10% sodium dodecyl sulphate (SDS) was added, the solution mixed and placed at 65° C. for 10 minutes. 10 mg of pronase (82 U/mg, CalBiochem) was added and the solution incubated at 50° C. until clearing of the solution occurred. 95% ethanol was slowly added and the DNA was spooled around a small glass rod. The DNA was redissolved in 5 ml TES (50 mM NaCl, 30 mM Tris-HCl, pH 7.5, 5 mM EDTA). The DNA solution was extracted twice with equal volumes of phenol, 95% ethanol precipitated using 95% ethanol and dissolved in 2 ml TES. RNase A (50 μg/ml) and T$_1$ (1 U/ml) obtained from Boehringer Mannheim were added and the solution incubated at 37° for 30 minutes. The DNA was spooled two or more times and resuspended in 1 ml of TE (10 mM Tris-HCl pH 7.5, 1 mM EDTA). 500 μg of total DNA from B. cereus 569H was isolated.

B. Isolation of Plasmid Vector DNA (pBD214)

BD843, a B. subtilis strain (BD393) carrying plasmid pBD214 as described by Gryczan, T. J. and Dubnau, D. (1982) Gene 20, 459–469 which is incorporated herein by reference, was grown overnight in 1 liter of VY; Dubnau, D., et al. (1969) J. of Mol. Biology 45, 155–179+5 μg/ml chloramphenicol (Cm). The cells were centrifuged at 5000 rpm for 10 minutes and washed in 50 ml of TES. The cells were again centrifuged at 5000 rpm for 5 minutes and the pBD214 plasmid DNA was isolated according to the following modified method described by Birnboim, H. C. and Doly, J. (1979) Nucleic Acids, Res. 7, 1513-1523. The cells were resuspended in 40 ml of 100 mM Tris-HCl pH 8, 20 mM EDTA. Lysozyme was added to a final concentration of 0.2 mg/ml. The resulting solution was incubated at 37° for 15 minutes. 80 ml of 1% SDS, 0.2N NaOH was added and the solution mixed gently. 60 ml of 3M NaOAc, pH 5 was then added and the solution was gently shaken again. The solution was then placed at $-20°$ C. for 1 hour and centrifuged at 10,000 rpm for 30 minutes in order to spin out cell debris. The supernatant was then carefully removed and to it was added 2 volumes of 95% ethanol at room temperature. The solution was centrifuged at 10,000 rpm for 15 minutes. The nucleic acid pellet was then resuspended in 5 ml TES. RNase A (50 μg/ml) and $T_1$ (1 U/ml) were added and the solution incubated at 37° for 30 minutes. The DNA was then precipitated with the addition of 1/10 vol 3M NaOAc at pH 5, and 2 volumes 95% ethanol. The solution was placed at $-20°$ C. for 2 hours. The total DNA was centrifuged at 10,000 rpm for 15 minutes and resuspended in 28 ml of TES and the plasmid DNA was purified by a cesium chloride continuous density gradient. Cesium chloride was added at a concentration of 1.1 g/ml and 4 ml of a 5 mg/ml solution of ethidium bromide was added. The DNA was centrifuged at 40,000 rpm for 40 hours in a Ti 50 rotor (Beckman). After centrifugation, the plasmid (lower) band in the gradient was visualized by UV light and collected with a syringe. The solution was extracted 3 times with cesium chloride saturated isopropanol and dialyzed against 4 liters of TE overnight. The pBD214 plasmid DNA was precipitated in 2 volumes of 95% ethanol. The final yield of pBD214 plasmid DNA was about 300-400 μg per liter of culture. This pBD214 plasmid DNA is to be used as the vector for the B. cereus DNA.

C. Construction of gene library from the 569H DNA

The construction of a B. subtilis gene library from the B. cereus 569H DNA obtained in Step A was accomplished using the system established by Gryczan, T. J. and Dubnau, D, 1982, and described in U.S. patent application Ser. No. 445,975, filed Dec. 1, 1982. This system is a positive selection system for plasmids that have DNA inserts. Cloning into the thy gene in the pBD214 plasmid inactivates it and when transformed into a thy$^-$ recipient (BD393 as defined in Table I of patent application No. 445,975) it confers trimethoprim (Tmp) resistance (Tmp$^r$). Plasmids that do not have inserts do not confer this resistance. By selecting for Tmp$^r$, Cm$^r$ (resistance to chloramphenicol), a pBD214 plasmid with an insert can always be detected.

The 2 μg of pBD214 DNA from step B and 6 μg of the B. cereus 569H DNA from step A were digested together with EcoRl restriction enzyme (Boehringer Mannheim). The digested DNA mixture was then extracted with an equal volume of a solution of 50:50 phenol:$CHCl_3$ and precipitated with two volumes of 95% ethanol. The digested DNA mixture was then ligated in 20 mM Tris-HCl pH7.5, 10 mM $MgCl_2$, 10 mM dithiothreitol, 1 mM ATP (Boehringer Mannheim) plus 5 units of T4 ligase (Boehringer Mannheim). The reactions were performed at 16° C. for 18 hours at a DNA concentration of 200 μg/ml. The ligated DNA was then reserved and used to transform a competent culture of BD393. Transformation of a culture is defined as introduction of an exogenous (foreign) DNA into a cell causing it to acquire a new phenotype.

A culture of BD393 was grown overnight in SPIZ I medium and was used to inoculate 50 ml of SPIZ II in order to prepare competent cells by the method described by Dubnau, D. and Davidoff-Abelson, R. (1971) J. Mol. Biol. 58, 209–221. The culture was shaken vigorously at 37° C. until a Klett reading of 180 was reached. 50 ml of cells were then added to 450 ml of SPIZ II. SPIZ I and SPIZ II media are described in Anagnostopoulos, C. & Spizizen, J. (1961) J. Bact. 81, 741–753. The culture was shaken for 2 hours at 37° C., and the cells were then centrifuged for 10 minutes at 15,000 rpm. The cells were resuspended in 45 ml SPIZ II and 5 ml of glycerol was added and the cells frozen at $-70°$ C.

The transformation of these competent cells was performed according to the following method described by Contente, S. and Dubnau, D. (1979) Mol. Gen. Genet. 167, 251-258. 0.5 ml of the frozen competent BD393 cells described above were thawed and to these cells 0.5 ml SPIZ II, 2 mM EGTA (Ethyleneglycol-bis-N,N'-tetraacetic acid) and 20 μl of the ligated 569H DNA/pBD214 DNA were added. The cells were incubated for 30 minutes at 37° C. with gentle mixing. 0.1 ml of this mixture was then plated on tryptose blood agar base plates (Difco) containing 5 μg/ml Tmp, 5 μg/ml Cm, 0.75% polyvinyl alcohol (PVA) and 50 μg/ml Trp, Lys and Thyd. Approximately 5,000 Tmp$^r$, Cm$^r$ clones were obtained. Each clone was believed to contain a different segment of the digested B. cereus 569H DNA ligated to the pBD214 vector.

D. Screening the B. cereus gene library to obtain the clone containing the gene which codes for penicillinase A plate assay to detect which of the clones from step C were synthesizing penicillinase was performed according to the method described by Sherratt, D. J. and Collins, J. F. (1973), Gen. Microbiol. 76, 217–230. Each colony was replica plated and one plate from each replicate set was flooded with a solution containing 0.08N $I_2$, 0.32N KI, and 1% sodium borate, for 30 to 60 seconds. The iodine solution was removed and the plates were then flooded with 1% pencillin G in 1 X SS; Anagnostopoulos, C. and Spizizen, J. (1961) J. Bact. 81, 741–753. The appearance of a clear halo surrounding a colony indicated that penicillinase was being produced by the colony. Three of the 5000 Tmp$^r$, Cm$^r$ colonies obtained from step C gave a positive response for penicillinase.

E. Stabilization of the penicillinase producing clones

In order to insure than a gene which coded for penicillinase was obtained, the clones which gave positive penicillinase results were further purified. The three positive clones described in D above were restreaked onto the same media and again tested for penicillinase activity. It was then found that only a very small percentage of the new colonies (0.1%) retained the penicillinase producing activity.

In order to further stabilize the penicillinase activity of the clones, the plasmid DNA was isolated from a positive clone according to the method described above (step A) except that a 10 ml culture (VY+5 g/ml CM) was used. The plasmid DNA was then used to transform new cultures of BD393 as described in step C. Penicillinase positive colonies were selected, the DNA isolated and used again to transform additional cultures of BD393. The same method was repeated until the number of colonies of transformed BD393 producing penicillinase increased.

When the percentage of colonies producing penicillinase became 1-10%, the plasmid DNA was prepared from cultures of the penicillinase positive colonies and used to transform cultures of IS75 selecting for $Cm^r$. IS75 is a competent *B. subtilis* strain described by Okubo, S. et al (1972) Biken, J. 15, 81–97. 10–20% of the transformed IS75 colonies obtained were penicillinase producers. Plasmid DNA was prepared from one of the transformed IS75 colonies that was producing penicillinase and used to again transform a new IS75 culture. This time 100% of the colonies of transformed IS75 were penicillinase producers. Restreaking of the transformed colonies showed that the clone was competely stable and continued to produce penicillinase. Plasmid DNA was prepared from a culture of transformed IS75 cells and identified as pAS7. IS75 cells carrying pAS7 have been designated AS10 and the strain deposited with the American Type Culture Collection, Rockville, Md. 20852. The deposited strain has been assigned ATCC number 39367.

F. Restriction Analysis and DNA Sequencing of the pAS7

In order to locate the regulatory elements, plasmid pAS7 DNA which was believed to contain the gene coding for penicillinase was digested with the restriction enzyme EcoR1 (Boehringer Mannheim) and electrophoresed on a 0.8% agarose gel. The pAS7 plasmid DNA as defined in E above was shown to have an insert of 4.3 Kb (kilobase pairs). The 4.3 Kb insert was mapped with other enzymes as shown in FIG. 1. The plasmid insert was shown to have two unique HindIII sites. Taking advantage of this, a plasmid that was missing the 556 base pair (b.p.) internal HindIII fragment was constructed and checked for activity. 2 μg of pAS7 DNA were digested with HindIII and religated under conditions described above. The ligated DNA was used to transform cells of IS75. Selecting for $Cm^r$, 250 colonies resulted. Both penicillinase positive and negative phenotypes resulted. Plasmid DNA was prepared from both sources. Restriction analysis of each revealed that the positive phenotype gave the same mapping pattern as pAS7, while the negative phenotype was lacking the internal HindIII fragment. This indicated that part of the structural gene or regulatory elements of the penicillinase gene in pAS7 were coded by the internal HindIII fragment. Therefore the HindIII sites were used to begin DNA sequencing of the gene.

G. DNA Sequence of the penicillinase gene

The nucleotide sequence of the gene which codes for penicillinase contained on the pAS7 plasmid was determined by the method of Maxam, A. M. and Gilbert, W. (1980) Methods Enzymol. 65, 499–560. The sequence of the entire structural gene and regulatory elements is shown in FIG. 2, and indicates a protein of 306 amino acids. The abbreviations used in the Figures have the following standard meanings:

A=deoxyadenyl
T=thymidyl
C=deoxycytosyl
G=deoxyguanyl
GLY=glycine
VAL=valine
ALA=alanine
LEU=leucine
ILE=isoleucine
SER=serine
THR=threonine
PHE=phenylalanine
TYR=tyrosine
TRP=tryptophan
CYS=cysteine
MET=methionine
ASP=aspartic acid
GLU=glutamic acid
LYS=lysine
ARG=arginine
HIS=histidine
PRO=proline
GLN=glutamine
ASN=asparagine FIG. 3 shows the 5' end of the novel gene which codes for penicillinase its promoter and signal peptide, Shine-Dalgarno (ribosome binding site) sequence, and the translational start codon.

H. Modification of signal sequence in the penicillinase gene

Prokaryotic genes whose DNA has been sequenced reveal that most signal peptides are cleaved after an alanine residue. The *B. licheniformis* penicillinase is cleaved after the alanine at the 34th amino acid as reported by Neugebauer, K. Sprengel, R. and Schaller, H. (1981) Nucleic Acids Res. 9, 2577–2588. It is likely that the position of cleavage of the *B. cereus* penicillinase gene coded by pAS7 is located after the alanine at the 37th amino acid.

Figure 4:
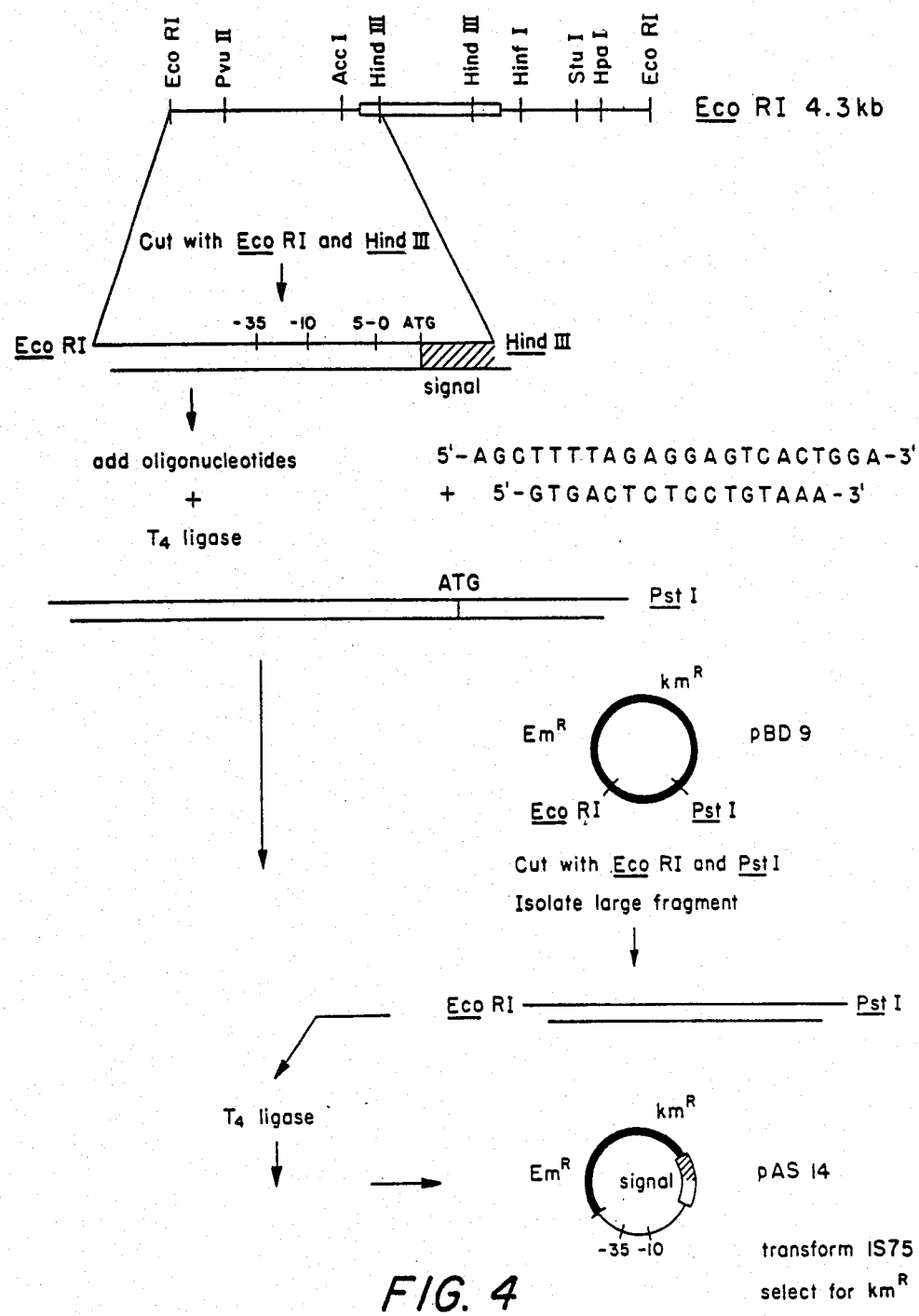
FIG. 4 shows schematically the formation of pAS14.
Figure 5:
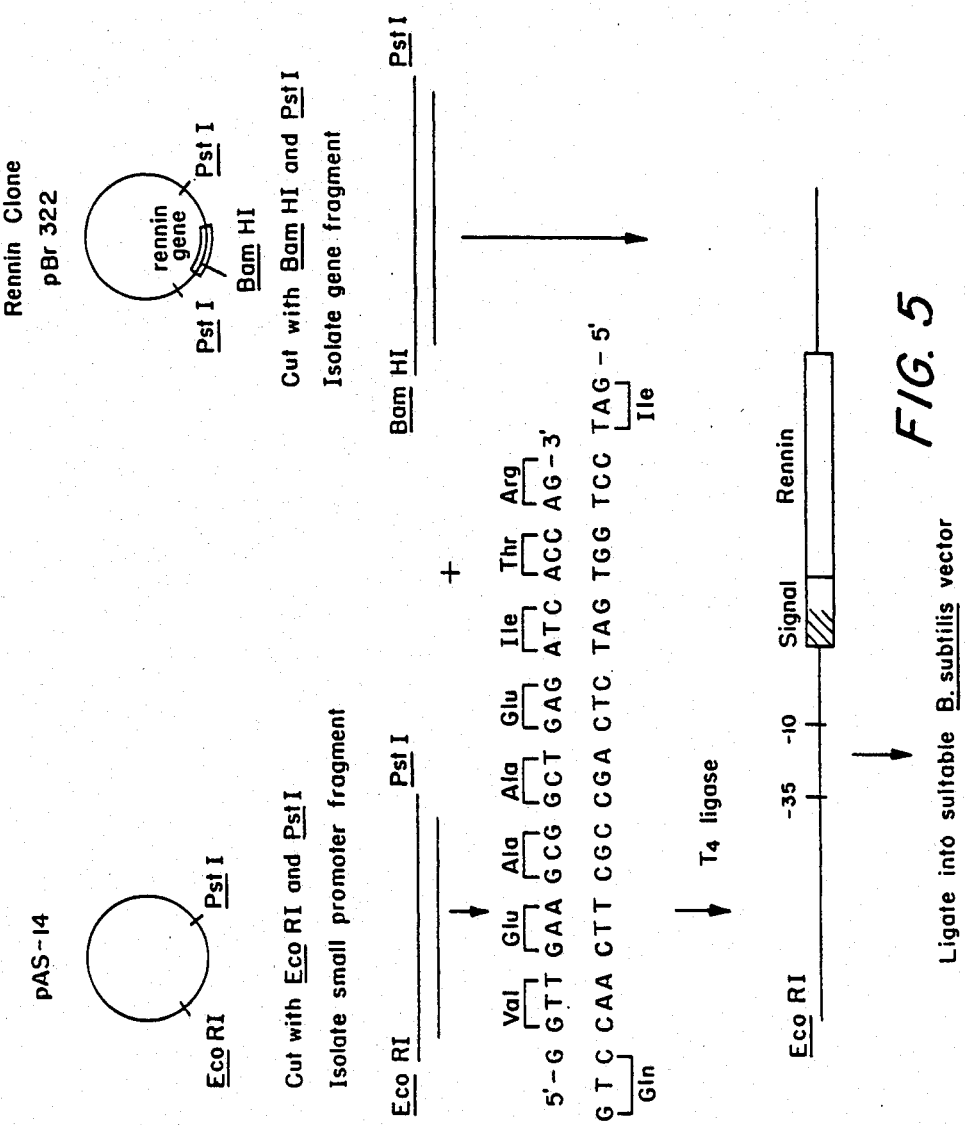
FIG. 5 shows schematically the linkage of a heterologous gene with pAS14.
Figure 6:
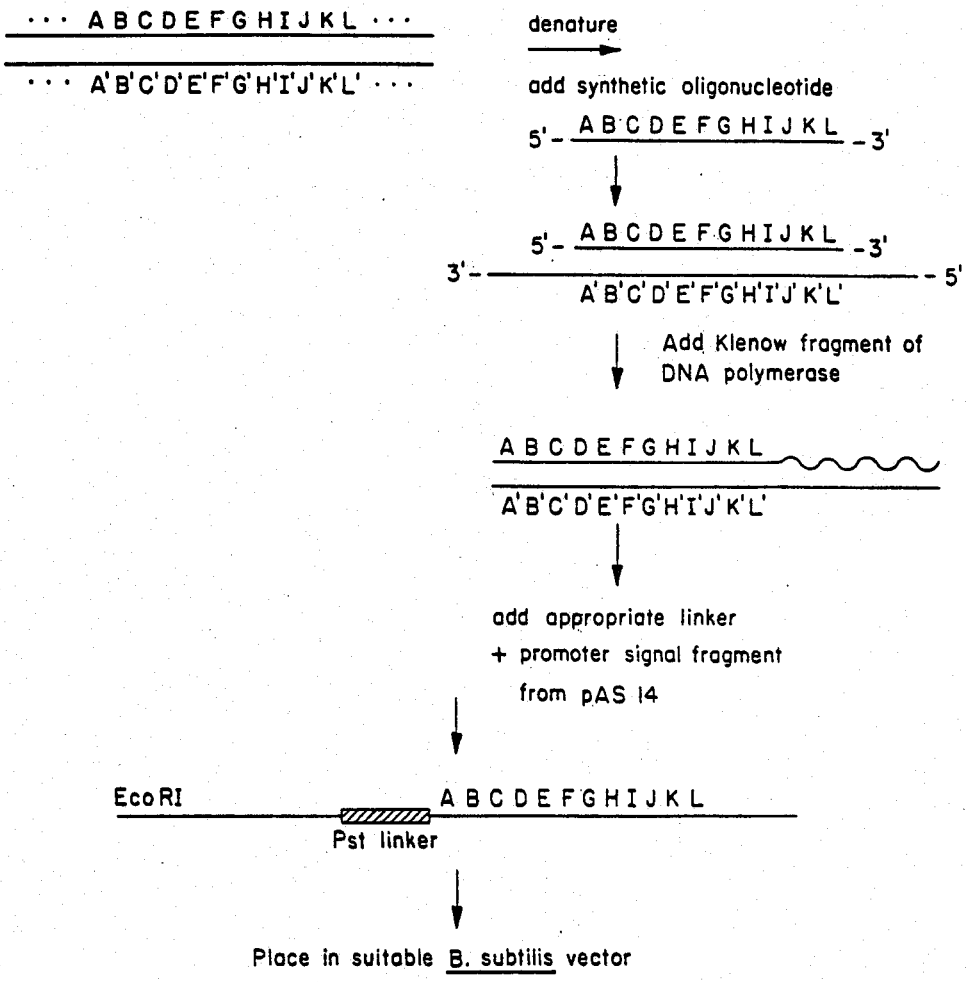
FIG. 6 shows schematically the modification of a heterologous gene to make it suitable for linkage with the plasmid.

In order to create a viable secretion vector from pAS7, it was necessary to isolate the gene from pAS7 which codes for penicillinase and to construct or identify a restriction site at or near the end of the signal sequence which allows for the linking, in phase, of one or more foreign or heterologous gene which code for one or more exogenous polypeptides (FIG. 4).

Digestion of pAS7 DNA with a HindIII restriction enzyme was used to cleave the pAS7 DNA in the signal peptide at amino acid numbers 26-27. The ligation of synthetic oligonucleotides 5'-AGCTTTTAGAG-GAGTCACTGGA-3' and 5'-GTGACTCTCCT-GTAAA-3' extends the signal to amino acids 33-34 and places a unique PstI site on the gene fragment at the position without changing any of the amino acids of the signal. The codon for GLN at amino acid 34 was changed from CAA to CAG.

The HindIII site in the signal sequence can also be used to link one or more foreign or heterologous genes. In this case, longer oligonucleotide are need to reconstruct the end of the signal sequence.

Oligonucleotides were synthesized chemically by the phosphate triester method described in Matteucci, M. D., and Caruthers, M. (1981) J.A.C.S. Vol. 103, 3185-97; Beaveage, S. C. and Caruthers, M. (1981) Tetrahedron Letters, Vol. 22, 1859–1874. This method permits the rapid synthesis of any defined nucleotide sequence and length Using the method of Gryczan, T. J. and Dubnau, D. (1978) Proc. Nat. Acad. Sci. USA 75, 1428–1432, the newly modified signal sequence and promoter sequence was then inserted in to a high-copy *B. subtilis* plasmid with EcoRl and PstI cloning sites such as pBD9. The resulting plasmid has been designated pAS14 and the strain (AS20) carrying the plasmid (pAS14) was deposited with the American Type Culture Collection, Rockville, Md. 20852. The deposited strain has been assigned ATCC number 39498. (FIG. 4).

I. Linkage of heterologous gene

A heterologous gene can be linked to the *B. cereus* penicillinase promoter and signal sequence produced herein but the method of linking depends on the available restriction sites in the DNA coding of the gene of the mature protein to be expressed. If there is a restriction site at or near the start of the heterologous gene to be linked to the novel penicillinase promoter and signal sequence, oligonucleotides are used to join the PstI or HindIII site from the signal to the start of the heterologous gene. An example of this method for calf rennin is shown in FIG. 5. This method could also be used for example to produce growth hormone, plasminogen activator or α-interferon. The gene coding for calf rennin has been cloned in *E. coli* by Harris, T. J. R. et al. (1982) Nucleic Acids Res. 10, 2177–2187 and has a Bam HI site at amino acid 4-5 of the mature calf rennin protein. Therefore, linkers are constructed that code for the last 3-4 amino acids of the penicillinase signal and the first 4-5 amino acids of calf rennin. (See FIG. 5)

If no restriction site exists at the start of the mature protein, the use of a oligonucleotide and the Klenow fragment of DNA polymerase results in the DNA starting at the first amino acid of the mature gene (FIG. 6) using the technique described by Goeddel, D. V. et al. (1980), Nucleic Acids Res. 8, 4057–4074. This method would be applicable for example to β-interferon and human serum albumin.

One of these methods could also be used to produce Factor VIII and urokinase. Once a suitable heterologous gene which codes for one or more exogenous polypeptides is linked to the novel penicillinase promoter and to a suitable plasmid, the vector is used to transformed a microorganism host such as *B. subtilis.* The transformed microorganism which secretes the exogenous polypeptide will be cultured and maintained under condition to optimize the polypeptide production.

I claim:

1. A vector which comprises the promoter sequence and at least a part of the signal sequence of the *Bacillus cereus* gene which codes for penicillinase in a plasmid capable of replicating in a host microorganism, wherein said part of the signal sequence encodes at least the first twenty-six amino acids of the signal peptide of *Bacillus cereus* penicillinase, said signal sequence having a restriction site at or near the 3′ end of the signal sequence to which one or more heterologous genes which code for one or more exogenous polypeptides can be linked.

2. A vector according to claim 1 wherein the restriction site is selected from the group consisting of a Pst I site and a Hind III site.

3. A vector according to claim 1 wherein the restriction site is constructed by addition of an oligonucleotide to the 3′ end of a restriction fragment comprising the promoter sequence and said part of the signal sequence.

4. A vector according to claim 3, wherein the 3′ end of the restriction fragment is a Hind III site.

5. A vector according to claim 4, wherein oligonucleotide sequences 5′-AGCTTTAGAGGAGTCACTGGA-3′ and 5′-GTGACTCTCCTGTAAA-3′ are ligated to the 3′ end of the restriction fragment.

6. A vector according to claim 1, wherein the heterologous genes code for one or more exogenous polypeptides selected from the group consisting of Urokinase, growth hormone, plasminogen activator, α-interferon, β-inteferon, calf rennin and human serum albumin.

7. The plasmid pAS7.

8. The plasmid pAS14.

9. A method of obtaining one or more exogenous polypeptides in the medium of a host microorganism which comprises:

linking one or more heterologous genes coding for one or more exogenous polypeptides with a vector capable of replicating in the host, said vector containing the promoter sequence and at least a part of the signal sequence of the *Bacillus cereus* gene coding for penicillinase, wherein said part of the signal sequence encodes at least the first twenty-six amino acids of the signal peptide of *Bacillus cereus* penicillinase, and said signal sequence having a restriction site near the 3′ end of the signal sequence at which the heterologous genes are linked;

transforming the host microorganism with the linked vector; and growing the transformed host in a suitable growth medium to produce exogenous polypeptides.

10. A method according to claim 9, wherein the restriction site is selected from the group consisting of a Pst I site and a Hind III site.

11. A method according to claim 10, wherein the restriction site is constructed by addition of an oligonucleotide to the 3′ end of a restriction fragment comprising the promoter sequence and said part of the signal sequence.

12. A method according to claim 9 wherein the vector is pAS14.

13. A method according to claim 9, wherein the host is *Bacillus subtilis.*

14. A method of constructing an expression and secretion vector comprising:

(a) cleaving a vector containing the *Bacillus cereus* gene coding for penicillinase with Eco RI and Hind III;

(b) isolating a restriction fragment containing the penicillinase promoter sequence and at least a part of the signal sequence, wherein said part of the signal sequence encodes at least the first twenty-six amino acids of the signal peptide of *Bacillus cereus* penicillinase;

(c) ligating an oligonucleotide to the 3′ ends of the restriction fragment to form a modified fragment such that a complete signal sequence and a restriction site at or near the 3′ end for the attachment of one or more heterologous genes coding for one or more exogenous proteins are present in the modified fragment;

(d) inserting the modified fragment containing the signal sequence and the promoter sequence into a plasmid capable of replicating in a host microorganism.

15. A method according to claim 14 wherein the vector in step (a) is pAS7.

16. A method according to claim 14 wherein the restriction site for the attachment of heterologous genes is selected from the group consisting of Eco RI, Pst I and Hind III.

* * * * *

UNITED STATES PATENT AND TRADEMARK OFFICE
CERTIFICATE OF CORRECTION

PATENT NO. : 4,663,280

DATED : May 5, 1987

INVENTOR(S) : Sloma

It is certified that error appears in the above-identified patent and that said Letters Patent is hereby corrected as shown below:

Col. 10, line 8, "5'-AGCTTTAGAGGAGTCACT-" should read --5'-AGCTTTTAGAGGAGTCACT- --.

Signed and Sealed this

Twelfth Day of July, 1988

Attest:

DONALD J. QUIGG

*Attesting Officer*  *Commissioner of Patents and Trademarks*